US006635414B2

(12) United States Patent
Wisniewski

(10) Patent No.: US 6,635,414 B2
(45) Date of Patent: *Oct. 21, 2003

(54) CRYOPRESERVATION SYSTEM WITH CONTROLLED DENDRITIC FREEZING FRONT VELOCITY

(75) Inventor: Richard Wisniewski, San Mateo, CA (US)

(73) Assignee: Integrated BioSystems, Inc., Napa, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/863,126

(22) Filed: May 22, 2001

(65) Prior Publication Data

US 2002/0177119 A1 Nov. 28, 2002

(51) Int. Cl.⁷ .............................. A01N 1/00; A01N 1/02; C12N 1/04; C12N 5/00; C12N 5/02
(52) U.S. Cl. .................... 435/1.3; 485/260; 485/325
(58) Field of Search ................................. 435/325, 180, 435/DIG. 19, 39, 284, 35, 1.3

(56) References Cited

U.S. PATENT DOCUMENTS

| | | |
|---|---|---|
| 876,015 A | 1/1908 | Ray |
| 983,466 A | 2/1911 | Vorhees |
| 1,874,578 A | 8/1932 | Morrison |
| 2,085,924 A | 7/1937 | Riegler |
| 2,129,572 A | 9/1938 | Finnegan |
| 2,391,876 A | 1/1946 | Brown |
| 2,405,091 A | 7/1946 | Culbreth |
| 2,441,376 A | 5/1948 | Stiening |
| 2,449,343 A | 9/1948 | Torbensen |
| 2,605,620 A | 8/1952 | Taylor |
| 2,610,034 A | 9/1952 | Lundvall et al. |
| 2,662,520 A | 12/1953 | McMahon .................... 128/1 |
| 2,704,656 A | 3/1955 | Freer |
| 2,915,292 A | 12/1959 | Gross |
| 3,074,246 A | 1/1963 | Wilbushewich |
| 3,108,840 A | 10/1963 | Conrad et al. |
| 3,121,627 A | 2/1964 | Harris .......................... 62/58 |
| 3,308,552 A | 3/1967 | Kaufman et al. |
| 3,318,105 A | 5/1967 | Burroughs et al. |
| 3,453,416 A | 7/1969 | Mekjean |
| 3,550,393 A | 12/1970 | Euwema |
| 3,595,308 A | 7/1971 | Durdin |
| 3,595,908 A | 7/1971 | Lumbroso et al. |
| 3,764,780 A | 10/1973 | Ellis |
| 3,934,618 A | 1/1976 | Henderson |
| 3,959,981 A | 6/1976 | Anderson .................... 62/135 |
| 3,976,129 A | 8/1976 | Silver |
| 4,030,314 A | 6/1977 | Strehler et al. |
| 4,107,937 A | 8/1978 | Chmiel .......................... 62/64 |
| 4,200,148 A | 4/1980 | Friefeld et al. |
| 4,241,043 A | 12/1980 | Hetzel |
| 4,296,612 A | 10/1981 | Allo |

(List continued on next page.)

FOREIGN PATENT DOCUMENTS

| | | |
|---|---|---|
| AU | A 12751/83 | 10/1983 |
| AU | 18668/83 | 4/1984 |
| EP | 0 316 966 B1 | 5/1989 |
| EP | 0 618 413 A1 | 10/1994 |
| EP | 0 647 707 A | 4/1995 |
| FR | 758510 | 1/1934 |
| FR | 2237156 | 2/1975 |
| GB | 518301 | 2/1940 |
| GB | 845576 | 8/1960 |
| GB | 2 029 880 A | 8/1982 |
| GB | 2196830 A | 5/1988 |
| GB | 2240165 A | 7/1991 |
| GB | 2351799 A | 1/2001 |
| JP | 57-580587 | 4/1982 |
| WO | WO/9823907 | 6/1998 |

OTHER PUBLICATIONS

Burton et al., "An Experimental Investigation of the Solidification Process in a V–shaped Sump", Int. J. Heat Mass Transfer, vol. 38, No. 13 (1995), pp. 2383–2393.

Schwartz, H. W., "Production of Orange Juice Concentration and Powder", Industrial and Engineering Chemistry, vol. 40 No. 5 May 1948, pp. 938–944.

Wisniewski, R. et al., "Large–Scale Freezing and Thawing of Biopharmaceutical Drug Product", Biotech and Biopharm. Manufacturing, Processing and Preservation, Tinterpharm Press, Illinois, 1996, pp. 7–59.

Wisniewski, R. et al., "Large–Scale Freezing and Thawing of Biopharmaceutical Drug Product", Proceedings of the International Congress, 1992, pp. 132–140.

Lawler, Frank K., "Engineering Advances FREEZE–Concentration", Food Engineering, vol. 23, No. 10, Oct. 1951, pp. 68–71, 210–213.

Gore, H.C., "Apple Sirup and Concentrated Cider: New Products for Utilizing Surplus and Cull Apples.", Yearbook of the Department of Agricultre, 1914, pp. 227–244.

Stahl, A.L., "Construction of Citrus Juices by Freezing", Florida State Horticultural Society, 1944, pp. 43–45.

Kalhori, B. et al., "Studies on Heat Transfer From a Vertical Cylinder, With or Without Fins, Embedded in a Solid Phase Change Mediam", Transactions of the ASME, Journal of Heat Transfer, vol. 107, Feb. 1985, pp. 44–51.

Primary Examiner—David M. Naff
Assistant Examiner—Deborah F. Ware
(74) Attorney, Agent, or Firm—Heslin Rothenberg Farley & Mesiti P.C.

(57) ABSTRACT

A biopharmaceutical material cryopreservation system is provided that includes a flexible sterile container comprising a biocompatible polymeric material. The flexible sterile container contains biopharmaceuticals materials for freezing and cryopreservation. A freezing system is thermally coupled to the biopharmaceutical materials via the flexible sterile container. The freezing system comprises a temperature sensor that monitors a temperature of the biopharmaceutical materials. Also, the freezing system comprises a feedback loop constructed to control a dendritic freezing front velocity, within the biopharmaceutical materials, in a range from approximately 5 millimeters per hour to approximately 250 millimeters per hour based on feedback information from the temperature sensor.

34 Claims, 1 Drawing Sheet

U.S. PATENT DOCUMENTS

| | | |
|---|---|---|
| 4,304,293 A | 12/1981 | Scheiwe et al. |
| 4,337,079 A | 6/1982 | Mann, Jr. et al. |
| 4,344,479 A | 8/1982 | Bailey |
| 4,426,959 A | 1/1984 | McCurley |
| 4,490,982 A | 1/1985 | Christmas .................. 62/3 |
| 4,509,344 A | 4/1985 | Ludwigsen et al. |
| 4,512,388 A | 4/1985 | Claar et al. |
| 4,531,373 A | 7/1985 | Rubinsky |
| 4,537,034 A * | 8/1985 | Crouch .................. 62/62 |
| 4,580,409 A | 4/1986 | Angelier et al. |
| 4,584,843 A | 4/1986 | Pronger, Jr. et al. |
| 4,596,120 A | 6/1986 | Knodel et al. |
| 4,609,036 A | 9/1986 | Schrader |
| 4,712,607 A | 12/1987 | Lindeman et al. |
| 4,793,151 A | 12/1988 | Masel et al. |
| 4,893,670 A | 1/1990 | Joshi et al. |
| 4,976,308 A | 12/1990 | Faghri |
| 4,986,080 A | 1/1991 | Grigoli et al. .................. 62/75 |
| 5,005,371 A | 4/1991 | Yonezawa et al. |
| 5,022,149 A | 6/1991 | Abbott |
| 5,029,634 A | 7/1991 | Hurner |
| 5,033,544 A | 7/1991 | Abbott |
| 5,054,548 A | 10/1991 | Zohler |
| 5,072,569 A | 12/1991 | VanTassel |
| 5,090,207 A | 2/1992 | Gilbertson et al. |
| 5,168,725 A | 12/1992 | Margolin |
| 5,176,197 A | 1/1993 | Hamaguchi et al. |
| 5,181,387 A | 1/1993 | Meckler |
| 5,212,957 A | 5/1993 | Ruff |
| 5,220,954 A | 6/1993 | Longardner et al. |
| 5,332,034 A | 7/1994 | Chiang et al. |
| 5,374,436 A | 12/1994 | White et al. .................. 426/249 |
| 5,411,078 A | 5/1995 | Ares |
| 5,458,191 A | 10/1995 | Chiang et al. |
| 5,476,763 A | 12/1995 | Bacchi et al. |
| 5,520,885 A | 5/1996 | Coelho et al. |
| 5,524,706 A | 6/1996 | Nakamura et al. |
| 5,524,990 A * | 6/1996 | Buck .................. 383/34 |
| 5,535,598 A | 7/1996 | Cothern et al. |
| 5,579,830 A | 12/1996 | Giammaruti |
| 5,582,856 A | 12/1996 | White et al. .................. 426/249 |
| 5,644,922 A | 7/1997 | Linden et al. |
| 5,863,715 A | 1/1999 | Rajotte et al. |
| 5,873,254 A * | 2/1999 | Arav .................. 62/63 |
| 6,196,296 B1 * | 3/2001 | Wisniewski et al. .......... 165/47 |
| 6,220,038 B1 | 4/2001 | Marsh et al. .................. 62/71 |

* cited by examiner

CRYOPRESERVATION SYSTEM WITH CONTROLLED DENDRITIC FREEZING FRONT VELOCITY

BACKGROUND OF THE INVENTION

1. Field of the Invention

This invention relates to biopharmaceutical material cryogenic preservation methods and apparatus, and more particularly to a biopharmaceutical material cryogenic preservation system and method which maintains a controlled dendritic freezing front velocity.

2. Description of Related Art

Cryopreservation of biopharmaceutical materials is important in the manufacturing, use, storage and sale of such products. For example, biopharmaceutical materials are often cryopreserved by freezing between processing steps and during storage. Similarly, in certain cases, biopharmaceutical materials are frozen and thawed as part of the development process to enhance their quality or to simplify the development process.

When utilizing cryopreservation, the overall quality, and in particular pharmaceutical activity, of the pharmaceutical products is desirably preserved, without substantial degradation of the biopharmaceutical products or solutes.

Currently, in some aspects, cryopreservation of biopharmaceutical materials involves disposing a container comprising the biopharmaceutical materials in a cabinet or chest freezer and allowing the biopharmaceutical materials to freeze. In current cryopreservation techniques, a container enclosing biopharmaceutical materials is placed on a solid or wire-frame shelf in the cabinet or chest freezer. The biopharmaceutical materials are left to freeze until they are solid, in an uncontrolled fashion.

The results from such freezing can be disappointing, to say the least. Significant losses in biopharmaceutical material activity have been noted. For example, observers have noted that stability and conformation of biopharmaceutical materials can be affected by low temperature alone, without any significant changes in variables such as solute concentration or pH.

Further, it has been noted that conventional cryopreservation methods can lead to cryoconcentration, or the redistribution of solutes from the frozen volume to the unfrozen cavity. The result of cryoconcentration can include the crystallization of buffer components leading to a pH change that can affect stability, folding, or even create cleavage of the biopharmaceutical material. Cryoconcentration in conjunction with low temperature effects may cause a decrease in solubility of the biopharmaceutical material, with resulting precipitation.

Finally, damage to the containers has been noted using conventional cryopreservation techniques. Rupture or damage to the integrity of the container is undesirable, as it can compromise sterility or lead to contamination and loss of the biopharmaceutical product.

Accordingly, there is a need for apparatus and methods for cryopreservation of biopharmaceutical materials that solve the deficiencies noted above.

SUMMARY OF THE INVENTION

In an aspect, the invention relates to a biopharmaceutical material cryopreservation system comprising a flexible sterile container comprising a biocompatible polymeric material, and the flexible sterile container containing biopharmaceuticals materials, and a freezing system thermally coupled to the biopharmaceutical materials via the flexible sterile container, and the freezing system comprising a temperature sensor that monitors a temperature of the biopharmaceutical materials wherein the freezing system comprises a feedback loop constructed to control a dendritic freezing front velocity, within the biopharmaceutical materials, in a range from approximately 5 millimeters per hour to approximately 250 millimeters per hour based on feedback information from the temperature sensor.

In another aspect, the invention relates to a method for cryopreservation of biopharmaceutical materials, comprising:

providing a flexible sterile container comprising a biocompatible polymeric material, and the flexible sterile container containing biopharmaceuticals materials; thermally coupling a freezing system to the biopharmaceutical materials via the flexible sterile container, and the freezing system comprising (i) a temperature sensor that monitors a temperature of the biopharmaceutical materials, and (ii) a feedback loop constructed to control a dendritic freezing front velocity; and controlling the dendritic freezing front velocity, within the biopharmaceutical materials, in a range from approximately 5 millimeters per hour to approximately 250 millimeters per hour based on feedback information from the temperature sensor.

In yet another aspect, the invention relates to a biopharmaceutical material cryopreservation system, comprising flexible sterile container means for counting biopharmaceutical products, and the flexible sterile container means comprising a biocompatible polymeric material, and the flexible sterile container containing biopharmaceuticals materials, and; freezing means for freezing the biopharmaceutical materials, and the freezing means thermally coupled to the biopharmaceutical materials via the flexible sterile container, and the freezing means comprising a temperature sensor that monitors a temperature of the biopharmaceutical materials wherein the freezing means comprises a feedback loop constructed to control a dendritic freezing front velocity, within the biopharmaceutical materials, in a range from approximately 5 millimeters per hour to approximately 250 millimeters per hour based on feedback information from the temperature sensor.

DETAILED DESCRIPTION OF THE INVENTION

Figure 1:
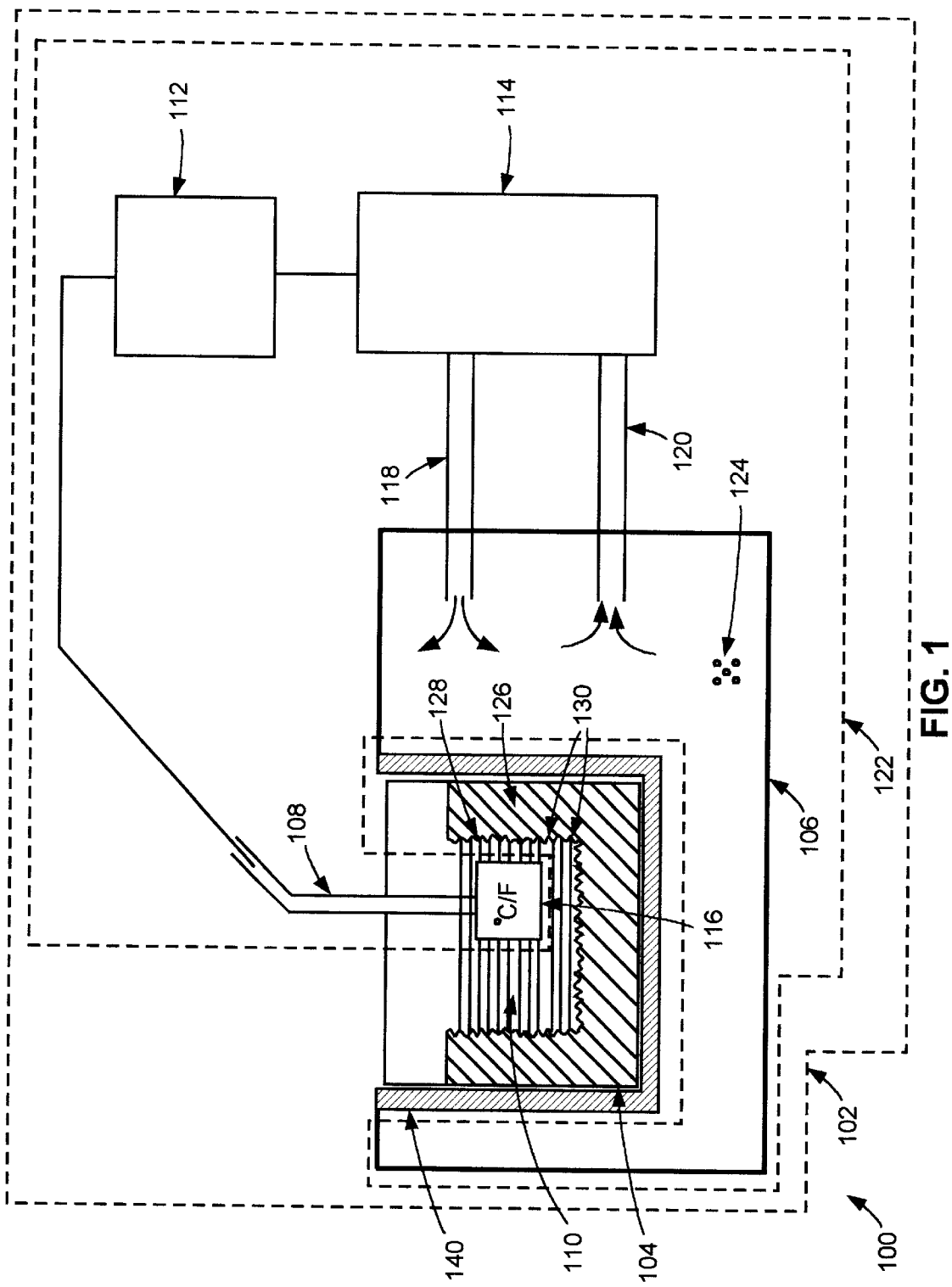
FIG. 1 shows a biopharmaceutical material cryopreservation system according to the present invention.

The inventor has unexpectedly discovered that controlling the freezing rate in cryopreservation and cryoprocessing of biopharmaceutical materials can solve the above-mentioned problems. According to an aspect of the present invention, the problems identified above may be partially or completely eliminated by ensuring that cryopreservation or cryoprocessing of biopharmaceutical materials is performed in a controlled manner such that the freezing rate of the biopharmaceutical materials is maintained within a desirable range.

When processing biopharmaceutical materials such as cells for cryopreservation, for example, if the cells are frozen too quickly, with too high of a water content, the cells may develop intracellular ice crystals. As a result, the cells may rupture and/or become unviable. On the other hand, if the cells are frozen too slowly, the cells are exposed to concentrated solutes over extended period of time, which may also lead to cell damage. As another example, freezing rate is also important in cryopreservation of protein solutions formulated for pharmaceutical use.

According to the present invention, maintaining the velocity of a dendritic ice crystal freezing front (hereafter "dendritic freezing front") in a range from approximately 5 millimeters per hour to approximately 250 millimeters per hour, or more preferably in a range from approximately 8 millimeters per hour to approximately 180 millimeters per hour, or most preferably in a range from approximately 10 millimeters per hour to approximately 125 millimeters per hour, provides advantageous cryoprocessing conditions in a wide range of systems and feasible operating margins so that damage to biopharmaceutical materials may be minimized or avoided.

As an example, the following discussion illustrates the relationship between the velocity of dendritic freezing front and the size and spacing of frozen dendrites in the context of freezing of biopharmaceutical materials.

If the velocity of the dendritic freezing front is much lower than approximately 5 millimeters per hour, the dendrites are small and densely packed within the dendritic freezing front. Consequently, the dendritic freezing front behaves as a solid interface with solutes and certain biopharmaceutical materials not being integrated into the solid mass. Instead, the solutes and biopharmaceutical materials are pushed forward by the advancing dendritic freezing front and their concentration in the substantially non-solid biopharmaceutical material phase increases. This "cryocentration" effect may result in damage to biopharmaceutical materials.

As the velocity of dendritic freezing front increases to, but still remains less than approximately 5 millimeters per hour, the dendrites grow somewhat larger in size and more separated, developing into cellular or columnar patterns. In this case, cryoconcentration may still occur, with only a small percentage of the solutes or biopharmaceutical materials become embedded into the solid mass. This situation may result in damaging of biopharmaceutical materials.

If the velocity of the dendritic freezing front is in a range from approximately 5 millimeters per hour to approximately 250 millimeters per hour, however, the dendrites grow sufficiently large and far apart to properly embed solutes and biopharmaceutical materials into the dendritic freezing front. One aspect of the present invention provides a method and apparatus for maintaining the velocity of dendritic freezing front in a range from approximately 5 millimeters per hour to approximately 250 millimeters per hour to provide proper conditions for cryopreservation and cryoprocessing of biopharmaceutical materials.

If the velocity of dendritic freezing front increases beyond approximately 250 millimeters per hour, dendrites start to decrease in size and become more compactly packed, thereby losing the ability to properly embed solutes and particles comprised in biopharmaceutical materials into freezing front.

If the velocity of the freezing front is much higher than approximately 250 millimeters per hour, the resulting solid mass comprises a random, unequilibrated, structure of fine ice crystals. Such rapid cryocooling could be achieved, for example, by supercooling small volumes of biopharmaceutical materials, by freezing biopharmaceutical materials in thin layers, or by submerging small volumes of biopharmaceutical materials into liquid nitrogen or other cryogenic fluid.

For example, in biopharmaceutical materials subjected to supercooling in a liquid phase followed by a rapid ice crystal growth, the velocity of the freezing front may exceed 1000 mm/sec. Such fast front velocities can create solid masses that comprise biopharmaceutical materials, wherein the solid masses are not formed of equilibrated ice crystals. These non-equilibrated solid masses are prone to ice recrystallization, when dissolution of smaller ice crystals and growth of larger ice crystals may impose excessive mechanical forces on biopharmaceutical materials. Further, biopharmaceutical materials in non-equilibrated solid masses may be distributed between ice crystals in very thin layers on grain boundaries. This produces a large product-ice contact interface area, which is detrimental to biopharmaceutical materials.

Inter-dendritic spacing can be regulated by increasing or decreasing the heat flux out of the system (thereby influencing thermal effects and the resulting front velocities), and by selection of solutes.

The length of free dendrites may depend in part on the front velocity and on the temperature gradient along the dendrites. The free dendrite may refer to the length of the dendrite sticking into the liquid phase, or, alternatively, the thickness of a "two-phase zone", e.g. a mixture of dendritic ice crystal needles and liquid phase between them. At the tips of the dendrites, the temperature is close to 0° C., and decreases gradually to match the wall temperature along the dendrite length and the solidified mass away from the front. The temperature of liquid between the dendrites also decreases with nearness to the cold wall. As cryocooling continues, with certain solutes such as salts, the solute concentration reaches a eutectic concentration and temperature. The solution between the dendrites then solidifies, reaching the complete or substantially complete, or solid, dendritic state. This state is a matrix of the dendritic ice crystals and solidified solutes in a eutectic state between those dendritic ice crystals. Dendritic ice crystals are described further in R. Wisniewski, *Developing Large-Scale Cryopreservation Systems for Biopharmaceutical Systems,* BioPharm 11(6):50–56 (1998) and R. Wisniewski, *Large Scale Cryopreservation of Cells, Cell Components, and Biological Solutions,* BioPharm 11(9):42–61 (1998), all of which are incorporated herein by reference.

An inventive apparatus designed to utilize the above understandings is shown in FIG. 1, which shows a biopharmaceutical material cryopreservation system according to the present invention. Biopharmaceutical material cryopreservation system 100 comprises system 102, flexible sterile container 104, cryocooling enclosure 106, aseptic port 108, biopharmaceutical materials 110, control system 112, cryorefrigeration system 114, temperature sensor 116, cryocoolant feeder 118, cryocoolant recirculator 120, freezing system 122, cryocoolant 124, solid mass 126, dendritic freezing front 128 and dendrites 130.

Structurally, flexible sterile container 104 is disposed within cryocooling enclosure 106. In a preferable embodiment, flexible sterile container 104 may be located within a cavity of optional additional container 140. In operation, optional additional container 140 serves to support flexible sterile container and permits heat transfer across its surfaces.

In an embodiment flexible sterile container 104 is pre-sterilized prior to being employed in cryopreservation or cryoprocessing of biopharmaceutical materials according to the present invention. If it is desirable to maintain sterility of the biopharmaceutical materials during processing, appropriate precautions must be observed in subsequent manipulation of pre-sterilized flexible sterile container 104.

Flexible sterile container 104 is comprised of a biocompatible polymeric material to promote relative compatibility with biopharmaceutical materials 110 and to avoid undesirable leaching of components from flexible sterile container 104 into biopharmaceutical materials 110. In the context of this application, biocompatible material characteristics involve benign interaction with biological products such that the structure, activity and efficacy of biopharmaceutical materials 110 are not negatively impacted and any viable cellular and tissue products are not exposed to toxic effects. Suitable biocompatible polymeric materials within the scope of the present invention comprise ethylene-vinyl acetate copolymer, ethylene-vinyl alcohol copolymer, polytetrafluoroethylene, polyethylene, polyesters, nylons, polypropylenes, polyvinylidenefluoride, polyurethanes, polyvinylchlorides, and mixtures or laminates that comprise the above.

Sterile flexible container 104 contains biopharmaceutical materials 110. Biopharmaceutical materials comprise those materials that are derived from biological sources that have an intended therapeutic application and whose manufacturing is or will be regulated by pharmaceutical or veterinary regulatory agencies. In an embodiment, biopharmaceutical materials 110 may comprise protein solutions, protein formulations, amino acid solutions, amino acid formulations, peptide solutions, peptide formulations, DNA solutions, DNA formulations, RNA solutions, RNA formulations, nucleic acid solutions, nucleic acid formulations, biological cell suspensions, biological cell fragment suspensions (including cell organelles, nuclei, inclusion bodies, and/or membranes), tissue fragments suspensions, cell aggregates suspensions, biological tissues in solution, organs in solution, embryos in solution, cell growth media, serum, biologicals, blood products, preservation solutions, fermentation broths, and cell culture fluids with and without cells, and mixtures of the above.

Flexible sterile container 104 may vary in size and may accommodate a wide range of biopharmaceutical material volumes. In a preferred embodiment, flexible sterile container 104 has a volumetric capacity in a range from approximately 20 milliliters to approximately 1000 liters, and more preferably in a range from approximately 500 milliliters to approximately 100 liters. In alternative preferred embodiments, flexible sterile container 104 has a volumetric capacity in a range from approximately 100 milliliters to approximately 500 milliliters, from approximately 1 liter to approximately 20 liters, or from approximately 0.5 milliliters to approximately 50 liters.

Biopharmaceutical materials 110 comprise solid mass 126, dendritic freezing front 128 and dendrites 130. Aseptic port 108 is mechanically coupled to the upper surface of flexible sterile container 104 and protrudes inside flexible container 104. In a preferred embodiment, aseptic port 108 comprises temperature sensor 116, which is immersed within biopharmaceutical materials 110. In an alternative preferred embodiment, temperature sensor 116 is disposed outside flexible sterile container 104 and comprises a temperature remote-sensing device. In a preferred embodiment, temperature sensor 116 comprises an infrared temperature sensing device. In an alternative embodiment, second aseptic port 108 is substantially inflexible and comprises temperature sensor 116.

In an embodiment, temperature sensor 116 is designed to function submerged into biopharmaceutical materials 110, thereby measuring the internal temperature of biopharmaceutical materials 110. In alternative embodiments, supplemental aseptic ports mechanically coupled to the upper surface of flexible sterile container 104 comprise temperature sensors that measure the internal temperature of biopharmaceutical materials 110 at additional points. In alternative embodiments, supplemental remote-sensing temperature sensors may be disposed outside flexible sterile container 104.

In alternative embodiments, supplemental aseptic ports are mechanically coupled to the upper surface of flexible sterile container 104 in addition to aseptic port 106, similarly protruding and extending into flexible sterile container 104. In a preferred embodiment, the supplemental aseptic ports include an aseptic port that permits introduction of biopharmaceutical materials 110 into flexible sterile container 104 or withdrawal of biopharmaceutical materials 110 from flexible sterile container 104. In alternative embodiments, the supplemental ports may include one or more of each of the following types of ports: filling ports, emptying ports, vent ports, sampling ports, additional temperature measuring ports (in a preferred embodiment comprising a capped tip), spectroscopic or light-based probe tube ports (in a preferred embodiment comprising a tip capped with a transparent or clear lens to accommodate a fiber optic spectroscopic probe) and others.

Flexible sterile container 104 exhibits structural flexibility. Structural flexibility means that walls of the flexible sterile container deform under the static head of the biopharmaceutical materials. In alternative embodiments, flexible sterile container 104 ranges in shape and structural characteristics from a soft-walled container which can be folded, or while empty collapses by itself, through a stiffer design which has flexible walls and can be stored in collapsed shape, but might maintain some of its own shape when empty, to a semi-rigid type, which can maintain its shape when empty and deforms partly only when filled with product (i.e., it possesses sufficient flexibility to adapt to the cryocooling walls shape). In certain preferred embodiments, surfaces of flexible sterile container 104 substantially conform to the shape of the optional additional container 140 with which the surfaces may be in physical contact and provide good surface contact for heat transfer.

In an embodiment, flexible sterile container 104 may be folded for storage or transportation and unfolded prior to being used for cryopreservation or cryoprocessing according to the present invention. In a related embodiment, aseptic port 108 and any additional aseptic ports coupled to flexible sterile container 104 exhibit various degrees of flexibility to facilitate the folding and unfolding of flexible sterile container 104 and may be folded together with flexible sterile container 104.

In a preferred embodiment, aseptic port 108 comprising temperature sensor 116 protrudes and extends into a substantially central area of flexible sterile container 104. An advantage of disposing aseptic port 108 comprising temperature sensor 116 in the substantially-central area of flexible sterile container 104 is that the portion of biopharmaceutical materials 110 located in this area may be the last to freeze, therefore maximizing the time available to temperature sensor 116 to measure the temperature of biopharmaceutical materials 110 in a substantially non-solid state.

In an alternative embodiment, aseptic port 108 is inflexible and is disposed in the substantially-central area of flexible sterile container 104. In this embodiment, flexible sterile container 104 may be folded longitudinally, along inflexible aseptic port 108 and any additional aseptic ports coupled to flexible sterile container 104.

Freezing system 122 comprises a feedback loop that comprises control system 112, cryorefrigeration system 114 and temperature sensor 116. Control system 112 is coupled to temperature sensor 116 and to cryorefrigeration system 114. In a preferred embodiment, control system 112 and cryorefrigeration system 114 are located outside cryocooling enclosure 106 and are coupled to cryocooling enclosure 102. In an alternative embodiment, cryocooling control system 112 may be disposed inside cryocooling enclosure 102, but outside flexible sterile container 104. In yet another embodiment, cryocooling control system 112 may be disposed inside aseptic port 108. In an alternative embodiment, cryocooling control system 112 may be disposed inside aseptic port 108 and may comprise temperature sensor 116.

Cryorefrigeration system 114 comprises cryocoolant feeder 118 and cryocoolant recirculator 120, which extend into cryocooling enclosure 106, thereby coupling cryorefrigeration system 114 with cryocooling enclosure 106. Cryocooling enclosure 106 comprises cryocoolant 124, which immerses flexible sterile container 104. In an embodiment, cryocoolant 124 may comprise air, liquid silicone heat transfer fluid, alcohol, freons, polyethylene glycol, or freezing salty brines (e.g. $CaCl_2$ brines).

As shown in FIG. 1, system 102 comprises cryocooling enclosure 106 and freezing system 122, and is adapted to receive flexible sterile container 104.

In operation, cryorefrigeration system 114 cools the internal volume of cryocooling enclosure 106 by removing heat from that volume. As cryorefrigeration system 114 removes heat from within cryocooling enclosure 106, the temperature inside cryocooling enclosure 106 but outside flexible sterile container 104 decreases. As a result, a temperature gradient develops between the cooler volume outside flexible sterile container 104 but inside cryocooling enclosure 106 and the warmer volume of biopharmaceutical materials 110. As a result of this temperature gradient, and because flexible sterile container 104 permits heat to be exchanged across its surfaces, heat is removed from biopharmaceutical materials 110, thereby cryocooling biopharmaceutical materials 110. Consequently, cryorefrigeration system 114 indirectly cools biopharmaceutical materials 110.

Cryorefrigeration system 114 feeds cryocoolant 124 into cryocooling enclosure 106 through cryocoolant feeder 118. The temperature of cryocoolant 124 can be either lower or higher than the temperature of biopharmaceutical materials 110, depending on whether biopharmaceutical materials 110 are being frozen or thawed. In a preferred embodiment, the temperature of cryocoolant 124 is lower than the temperature of biopharmaceutical materials 110 to cryogenically cool biopharmaceutical materials 110.

Cryorefrigeration system 114 recirculates cryocoolant 124 through cryocooling enclosure 106 by removing cryocoolant 124 through cryocoolant recirculator 120. In a preferred embodiment, when biopharmaceutical materials 110 are being cooled down, the temperature of cryocoolant 124 fed by cryorefrigeration system 114 into cryocooling enclosure 106 through cryocoolant feeder 118 is lower than the temperature of cryocoolant 124 removed through cryocoolant recirculator 120. Consequently, in this embodiment, cryorefrigeration system 114 processes cryocoolant 124 to decrease its temperature before feeding it back into cryocooling enclosure 106.

Cryorefrigeration system 114 can alter the rate and direction in which the temperature of biopharmaceutical materials 110 varies by either modifying the temperature differential between cryocoolant 124 fed into cryocooling enclosure 106 and cryocoolant 124 removed from cryocooling enclosure 106, or by altering the rate at which cryocoolant 124 is circulated through cryocooling enclosure 106. In a preferred embodiment, when biopharmaceutical materials 110 are being frozen, to increase the freezing rate of biopharmaceutical materials 110, cryorefrigeration system 114 increases the temperature differential between cryocoolant 124 fed into cryocooling enclosure 106 and biopharmaceutical materials 110 by further cryocooling down cryocoolant 124. In an alternative related preferred embodiment, cryorefrigeration system 114 achieves the same goal by maintaining the temperature differential between cryocoolant 124 fed into cryocooling enclosure 106 and cryocoolant 124 removed from cryocooling enclosure 106 unchanged, but instead increasing the rate at which it recirculates cryocoolant 124 through cryocooling enclosure 106 by increasing its speed through cryorefrigeration system 114.

In an alternative preferred embodiment, when biopharmaceutical materials 110 are being cooled down, to decrease the freezing rate of biopharmaceutical materials 110, cryorefrigeration system 114 decreases the temperature differential between cryocoolant 124 fed into cryocooling enclosure 106 and cryocoolant 124 removed from cryocooling enclosure 106 by decreasing the amount by which it cools down cryocoolant 124. In an alternative related preferred embodiment, cryorefrigeration system 114 achieves the same goal by maintaining the temperature differential between cryocoolant 124 fed into cryocooling enclosure 106 and cryocoolant 124 removed from cryocooling enclosure 106 unchanged, but instead decreasing the rate at which it recirculates cryocoolant 124 through cryocooling enclosure 106 by decreasing its speed through cryorefrigeration system 114.

Cryocoolant 124 is thermally coupled with the biopharmaceutical materials 110 via flexible sterile container 104 and its surfaces. In an embodiment, cryocoolant 124 exchanges heat with biopharmaceutical materials 110 directly through the surfaces of flexible sterile container 104. In an alternative embodiment, cryocoolant 124 is in direct contact with an optional additional container 140, which is thermally coupled with biopharmaceutical materials 110 through the surfaces of flexible sterile container 104. In this alternative preferred embodiment, cryocoolant 124 exchanges heat with the internal surfaces of the optional additional container, which exchanges heat with biopharmaceutical materials 110 through the surfaces of flexible sterile container 104. Consequently, in this alternative preferred embodiment, cryocoolant 124 exchanges heat with biopharmaceutical materials 110 indirectly. In an alternative preferred embodiment, cryocoolant 124 exchanges heat directly with biopharmaceutical materials 110, and exchanges heat indirectly with biopharmaceutical materials 110.

In an embodiment, by varying the temperature of cryocoolant 124 or the rate at which cryocoolant 124 is recirculated through cryocooling enclosure 106, cryorefrigeration system 114 controls the rate of cryocooling or warming of biopharmaceutical materials 110. In this preferred embodiment, temperature sensor 116 continuously monitors the temperature of biopharmaceutical materials 110 and transmits that information to control system 112. In an alternative embodiment, multiple temperature sensors are disposed within flexible sterile container 104 to measure the temperature of biopharmaceutical materials 110 at multiple locations. Cryorefrigeration system 114 measures the temperature of cryocoolant 124 as it enters and exits cryocooling enclosure 106 and transmits that information to control system 112. Control system 112 then directs cryorefrigeration system 114 to appropriately alter the flow rate of cryocoolant 124. Temperature sensor 116 acting together with control system 112 and cryorefrigeration system 114 produce therefore a feedback loop, which is comprised in feedback loop 122.

In a preferred embodiment, as cryocoolant 124 removes heat from flexible sterile container 104, the temperature of biopharmaceutical materials 110 decreases. Eventually, if this process continues for a sufficiently long period of time, a phase transition may commence within biopharmaceutical materials 110 in the proximity of the external surfaces of flexible sterile container 104. As the temperature of biopharmaceutical materials 110 continues to decrease, biopharmaceutical materials 110 freeze and solidify in the proximity of the surfaces of flexible sterile container 104, thereby producing solid mass 126. Depending on the particular shape of flexible sterile container 104, solid mass 126 may comprise multiple sub-fronts, which may be distributed along the surfaces of flexible sterile container 104 in thermal contact with surfaces of cryocooling enclosure 106 or with cryocoolant 124.

An important distinction between the present invention and conventional freezing techniques is that the present invention comprises a feedback loop that comprises the temperature of biopharmaceutical materials 110, rather than only the temperature of cryocoolant 124. For instance, conventional cabinet or chest freezers are so constructed as to have a feedback loop around the temperature of the air, which may serve as the cryocoolant, inside the cabinet or chest freezer. In this regard, little or no control is possible of the freezing fronts within any containers located in the cabinet or chest freezer. Variables such as location of the container within the cabinet or chest freezer, number of containers within the cabinet or chest freezer, wall thickness of the container, material of construction of the container, and other variables combine to make practical control of the freezing front within the container difficult or impossible.

In contrast, the present invention controls the rate of a dendritic freezing front velocity within biopharmaceutical materials 110 through fedback temperature information regarding biopharmaceutical materials 110 from temperature sensor 116. This feedback loop permits more precise control of heat removal from biopharmaceutical materials 110, and facilitates control of the dendritic freezing front velocity to within the recited ranges. Variables such as location within cryocooling enclosure 106, wall thickness of flexible sterile container 104, etc., are automatically taken into account through the feedback loop. Absent the feedback loop that comprises temperature of the biopharmaceutical materials 110, more precise control of the dendritic freezing front velocity would be practically difficult to accomplish.

Dendritic freezing front 128 separates solid mass 126 from substantially-non-solid biopharmaceutical materials 110, thereby producing a solid-liquid interface. As heat removal from biopharmaceutical materials 110 continues, dendritic freezing front 128 advanced away from the inner surface of flexible sterile container 104, as additional substantially-non-solid biopharmaceutical materials 110 freeze into solid mass 126. The dendritic freezing front velocity is the velocity with which a dendritic freezing front advances.

Consequently, in a preferred embodiment, the rate at which heat is removed from biopharmaceutical materials 110 determines the velocity of dendritic freezing front 128.

Since the temperature gradient between biopharmaceutical materials 110 and cryocoolant 124 is correlated with the rate at which heat is removed from biopharmaceutical materials 110, the velocity of dendritic freezing front 128 can be controlled by controlling the temperature of cryocoolant 124.

In a preferred embodiment, heat is removed from biopharmaceutical materials 110 at a rate that promotes a substantially uniform advance of dendritic freezing front 128 within substantially all volume of biopharmaceutical materials 110 or a substantially constant velocity of dendritic freezing front 128. Maintenance of a substantially constant velocity of dendritic freezing front 128 within flexible sterile container 104 according to an embodiment of this invention is desirable because it provides substantially steady-state conditions for undisturbed dendritic ice crystal growth, independently from the distance to the cooled heat transfer surface within the freezing volume.

It will be apparent to those skilled in the art that various modifications and variations can be made in the cryopreservation system components, systems and methods of the present invention without departing from the spirit or scope of the invention. Thus, it is intended that the present invention covers the modifications and variations of this invention provided they come within the scope of the appended claims and their equivalents.

What is claimed is:

1. A cryopreservation system, comprising:
   a biocompatible flexible container adapted to receive at least one biopharmaceutical material therein, and;
   a freezing system thermally coupled to the at least one biopharmaceutical material and/or the flexible container, said freezing system comprising a temperature sensor that monitors a temperature of the at least one biopharmaceutical material in the container,
   wherein the freezing system comprises a feedback loop constructed to control a dendritic freezing front velocity, within the at least one biopharmceutical material, in a range from approximately 5 millimeters per hour to approximately 250 millimeters per hour based on feedback information comprising the temperature detected by the temperature sensor.

2. The cryopreservation system of claim 1, wherein the biocompatible flexible container comprises ethylene-vinyl acetate copolymer, ethylene-vinyl alcohol copolymer, polytetrafluoroethylene, polyethylene, polyesters, nylons, polypropylenes, polyvinylidenefluoride, polyurethanes, polyvinylchlorides, or mixtures or laminates that comprise the above.

3. The cryopreservation system of claim 1, wherein the biocompatible flexible container possesses a volumetric capacity in a range from approximately 20 milliliters to approximately 1000 liters.

4. The cryopreservation system of claim 1, wherein the biocompatible flexible container possesses a volumetric capacity in a range from approximately 500 milliliters to approximately 100 liters.

5. The cryopreservation system of claim 1, wherein the biocompatible flexible container possesses a volumetric capacity in a range from approximately 100 milliliters to approximately 500 milliliters.

6. The cryopreservation system of claim 1, wherein the biocompatible flexible container possesses a volumetric capacity in a range from approximately 1 liter to approximately 20 liters.

7. The cryopreservation system of claim 1, wherein the biocompatible flexible container possesses a volumetric capacity in a range from approximately 0.5 milliliters to approximately 50 liters.

8. The cryopreservation system of claim 1, wherein the dendritic freezing front velocity is in a range from approximately 8 millimeters per hour to approximately 180 millimeters per hour.

9. The cryopreservation system of claim 1, wherein the dendritic freezing front velocity is in a range from approximately 10 millimeters per hour to approximately 125 millimeters per hour.

10. The cryopreservation system of claim 1, wherein the at least one biopharmaceutical material comprises protein solutions; protein formulations; amino acid solutions; amino acid formulations; peptide solutions; peptide formulations; DNA solutions; DNA formulations; RNA solutions; RNA formulations; nucleic acid solutions; nucleic acid formulations; biological cell suspensions; biological cell fragment suspensions including cell organelles, nuclei, inclusion bodies, and/or membranes; tissue fragments suspensions; cell aggregates suspensions; biological tissues in solution; organs in solution; embryos in solution; cell growth media; serum; biologicals; blood products; preservation solutions; fermentation broths; or cell culture fluids with and without cells; or mixtures of the above.

11. A method for cryopreservation of biopharmaceutical materials by freezing the materials, comprising:
providing a flexible container comprising a biocompatible material;
receiving at least one biopharmaceutical material in said container;
thermally coupling a freezing system to the at least one biopharmaceutical material and/or the flexible container, said freezing system comprising a temperature sensor that monitors a temperature of the at least one biopharmaceutical material in the container and a feedback loop constructed to control freezing; and
freezing said at least one biopharmaceutical material and controlling dendritic freezing front velocity during said freezing, within the at least one biopharmceutical material, in a range from approximately 5 millimeters per hour to approximately 250 millimeters per hour based on feedback information comprising the temperature detected by the temperature sensor.

12. The method of claim 11, wherein the biocompatible flexible container comprises ethylene-vinyl acetate copolymer, ethylene-vinyl alcohol copolymer, polytetrafluoroethylene, polyethylene, polyesters, nylons, polypropylenes, polyvinylidenefluoride, polyurethanes, polyvinylchlorides, or mixtures or laminates that comprise the above.

13. The method of claim 11, wherein the flexible container possesses a volumetric capacity in a range from approximately 20 milliliters to approximately 1000 liters.

14. The method of claim 11, wherein the flexible container possesses a volumetric capacity in a range from approximately 500 milliliters to approximately 100 liters.

15. The method of claim 11, wherein the flexible container possesses a volumetric capacity in a range from approximately 100 milliliters to approximately 500 milliliters.

16. The method of claim 11, wherein the flexible container possesses a volumetric capacity in a range from approximately 1 liter to approximately 20 liters.

17. The method of claim 11, wherein the flexible container possesses a volumetric capacity in a range from approximately 0.5 milliliters to approximately 50 liters.

18. The method of claim 11 wherein the dendritic freezing front velocity is controlled in a range from approximately 8 millimeters per hour to approximately 180 millimeters per hour based on feedback information from the temperature sensor.

19. The method of claim 11, wherein the dendritic freezing front velocity is controlled in a range from approximately 10 millimeters per hour to approximately 125 millimeters per hour based on feedback information from the temperature sensor.

20. The method of claim 11, wherein the at least one biopharmaceutical material comprises protein solutions; protein formulations; amino acid solutions; amino acid formulations; peptide solutions; peptide formulations; DNA solutions; DNA formulations; RNA solutions; RNA formulations; nucleic acid solutions; nucleic acid formulations; biological cell suspensions; biological cell fragment suspensions including cell organelles, nuclei, inclusion bodies, and/or membranes; tissue fragments suspensions; cell aggregates suspensions; biological tissues in solution; organs in solution; embryos in solution; cell growth media; serum; biologicals; blood products; preservation solutions; fermentation broths; or cell culture fluids with and without cells; or mixtures of the above.

21. A cryopreservation system, comprising:
flexible container means for receiving at least one biopharmaceutical material, said flexible container means comprising a biocompatible material, and;
freezing means for freezing the at least one biopharmaceutical material, said freezing means thermally coupled to the at least one biopharmaceutical material via the flexible container, said freezing means comprising a temperature sensor that monitors a temperature of the at least one biopharmaceutical material in the container,
wherein the freezing means comprises a feedback loop constructed to control a dendritic freezing front velocity, within the at least one biopharmaceutical material, in a range from approximately 5 millimeters per hour to approximately 250 millimeters per hour based on feedback information comprising the temperature detected by the temperature sensor.

22. The cryopreservation system of claim 21, wherein the biocompatible material comprises ethylene-vinyl acetate copolymer, ethylene-vinyl alcohol copolymer, polytetrafluoroethylene, polyethylene, polyesters, nylons, polypropylenes, polyvinylidenefluoride, polyurethanes, polyvinylchlorides, or mixtures or laminates that comprise the above.

23. The cryopreservation system of claim 21, wherein the dendritic freezing front velocity is in a range from approximately 8 millimeters per hour to approximately 180 millimeters per hour.

24. The cryopreservation system of claim 21, wherein the dendritic freezing front velocity is in a range from approximately 10 millimeters per hour to approximately 125 millimeters per hour.

25. The cryopreservation system of claim 21, wherein the at least one biopharmaceutical material comprise protein solutions; protein formulations; amino acid solutions; amino acid formulations; peptide solutions; peptide formulations; DNA solutions; DNA formulations; RNA solutions; RNA formulations; nucleic acid solutions; nucleic acid formulations; biological cell suspensions; biological cell fragment suspensions including cell organelles, nuclei, inclusion bodies, and/or membranes; tissue fragments suspensions; cell aggregates suspensions; biological tissues in solution; organs in solution; embryos in solution; cell growth media; serum; biologicals; blood products; preservation solutions;

fermentation broths; or cell culture fluids with and without cells; or mixtures of the above.

26. A cryopreservation system, comprising:
a biocompatible flexible container adapted to receive at least one biopharmaceutical material therein;
a freezing system thermally coupled to the at least one biopharmaceutical material and/or the flexible container, said freezing system comprising a cryocooling enclosure having an interior configured to receive and support said biocompatible flexible container, said cryocooler adapted to receive a cryocoolant therein to cool the interior of said crycooling enclosure;
one or more temperature sensors positioned to monitor a temperature relating to the at least one biopharmaceutical material in the container; and
a feedback loop constructed to control a dendritic freezing front velocity, within the at least one biopharmaceutical material, in a range from approximately 5 millimeters per hour to approximately 250 millimeters per hour based on feedback information comprising the temperature detected by the one or more temperature sensors.

27. The cryopreservation system of claim 1, wherein the temperature sensor is in said container.

28. The cryopreservation system of claim 1, wherein the temperature sensor is out of said container.

29. The method of claim 11, wherein the temperature sensor is in said container.

30. The method of claim 11, wherein the temperature sensor is out of said container.

31. The method of claim 21, wherein the temperature sensor is in said container.

32. The method of claim 21, wherein the temperature sensor is out of said container.

33. The method of claim 26, wherein one or more temperature sensors is in said container.

34. The system of claim 26, wherein one or more of said temperature sensors is out of said container.

* * * * *